United States Patent [19]

Baylis et al.

[11] 4,213,969
[45] Jul. 22, 1980

[54] PHOSPHONOUS ACID DERIVATIVES, PROCESSES FOR THEIR PREPARATION AND THEIR USE IN COMBATTING MICROORGANISMS

[75] Inventors: Eric K. Baylis; Wilfred Pickles, both of Stockport, England

[73] Assignee: Ciba-Geigy Corporation, Ardsley, N.Y.

[21] Appl. No.: 960,266

[22] Filed: Nov. 13, 1978

[30] Foreign Application Priority Data

Nov. 19, 1977 [GB] United Kingdom ............... 48264/77

[51] Int. Cl.² ................... A61K 37/100; C07C 103/52
[52] U.S. Cl. .............................. 424/177; 260/112.5 R; 260/502.5
[58] Field of Search ................. 260/112.5 R; 424/177; 260/502.5

[56] References Cited

U.S. PATENT DOCUMENTS 4,016,148  4/1977  Atherton et al. ............. 260/112.5 R

OTHER PUBLICATIONS

Huber, J., et al., Journal of Medicinal Chemistry, vol. 18, pp. 106–108, (1975).
Hariharan, M., et al., J. Org. Chem., vol. 40, pp. 470–473 (1975).
Gilmore, F., et al., J. Pharm. & Sci., vol. 63, 1087 (1974).

*Primary Examiner*—Delbert R. Phillips
*Assistant Examiner*—Blondel Hazel
*Attorney, Agent, or Firm*—Harry Falber

[57] ABSTRACT

Phosphonous acid derivatives of the general formula I

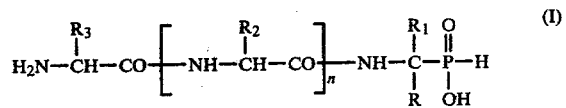

or the corresponding zwitterion form, in which R, $R_1$, $R_2$ and $R_3$ have the meanings given hereinafter, are valuable microbicides. They are being manufactured according to known methods of peptide synthesis and may be used to protect plants from the attack of plant-pathogenic bacteria and fungi.

33 Claims, No Drawings

PHOSPHONOUS ACID DERIVATIVES, PROCESSES FOR THEIR PREPARATION AND THEIR USE IN COMBATTING MICROORGANISMS

The present invention relates to phosphonous acid derivatives, especially to peptide phosphonous acid derivatives and to processes for their preparation, to compositions containing the new compounds as active ingredients and the use thereof.

The peptide derivatives provided by the present invention are compounds of the general formula I

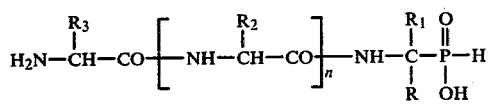

or the corresponding zwitterion form, in which

R and $R_1$ may be the same or different and each can be hydrogen, deuterium or an optionally substituted lower alkyl group, lower alkenyl, lower alkynyl, cycloalkyl, aryl or heterocyclic radical containing one or more oxygen, nitrogen or sulphur atoms and which may be fused to an aromatic ring, a lower alkyl group substituted by a cycloalkyl radical, a lower alkyl group substituted by an aryl radical, a lower alkyl group substituted by a heterocyclic radical as defined above, or R and $R_1$ together form a polymethylene chain optionally interrupted by an oxygen, nitrogen or sulphur atoms, or $R_1$ represents, together with the C(R)-N< residue to which it is attached, the atoms required to complete a heterocyclic radical; and $R_2$ and $R_3$ may be the same or different and each can be hydrogen, optionally substituted lower alkyl, cycloalkyl, aryl or lower alkyl substituted by a cycloalkyl radical, lower alkyl substituted by a heterocyclic radical containing one or more nitrogen atoms;

a heterocyclic radical containing one or more nitrogen atoms;

or $R_2$ and $R_3$, independently, together with the C(H)-N< residue to which each is attached, may each represent the atoms required to complete a heterocyclic radical; and n is 0, 1, 2 or 3; as well as the esters thereof with alcohols; salts of the compounds of formula I, or their esters, with acids or bases, respectively; and all optical isomers thereof. The α-amino acid residues or esters occurring in the peptides defined above may have the D,L-, L- or D- configuration.

The term "lower" referred to above and hereinafter in connection with organic radicals or compounds respectively, defines such with up to 6, preferably up to 3 carbon atoms.

The above listed radicals R, $R_1$, $R_2$ and $R_3$ optionally may be substituted by one or more functional groups, as for example, free or etherified hydroxy or mercapto groups, optionally converted carboxyl groups, S-substituted dithio groups, optionally substituted amino groups -$NR_4R_5$ in which $R_4$ and $R_5$ may be the same or different and can be hydrogen or lower alkyl or optionally substituted guanidino and/or optionally substituted aryl groups or heterocyclic residues.

Moreover R and $R_1$ as lower alkyl group, aryl group or heterocyclic radical or an aryl group or heterocyclic radical as substituent or R or $R_1$ as lower alkyl group may be substituted by one or more halogen atoms, -$NR_4R_5$ groups in which $R_4$ and $R_5$ together form a polymethylene chain containing up to 6 carbon atoms which may optionally be interrupted by oxygen or nitrogen or an aryloxy group optionally substituted by hydroxy or an halogen atom as for example iodine.

The substituents R, $R_1$, $R_2$ and $R_3$ as lower alkyl group may be straight or branched chain alkyl group of 1 to 6 carbon atoms and may be for example, methyl, ethyl, n-propyl iso-propyl, n-butyl, isobutyl, secondary butyl, tertiary butyl, n-amyl, isoamyl or n-hexyl. Preferred are lower alkyl groups of 1 to 3 carbon atoms as for example methyl, ethyl, n-propyl or isopropyl.

When R, $R_1$, $R_2$ or $R_3$ is a cycloalkyl group this may be a cycloalkyl group with 3 to 7 carbon atoms as for example a cyclopropyl, cyclobutyl, cyclopentyl, cyclohexyl or cycloheptyl group.

A lower alkyl group substituted by a cycloalkyl radical may be for example cyclopropyl-methyl, cyclopropyl-ethyl, cyclopropyl-n-propyl, cyclobutyl-methyl, cyclobutyl-ethyl, cyclobutyl-n-propyl, cyclopentyl-methyl, cyclopentyl-ethyl, cyclopentyl-n-propyl, cyclohexyl-methyl, cyclohexyl-ethyl, cyclohexyl-n-propyl, cycloheptyl-methyl, cycloheptyl-ethyl or cycloheptyl-n-propyl.

The term aryl preferably comprises mononuclear groups such as phenyl, which may be substituted in one or more positions by substituents such as lower alkyl, hydroxy, lower alkoxy or halogen.

Moreover in addition to the meaning above when R and $R_1$ or the substituent of a lower alkyl group thereof is an aryl group, this aryl group comprises 6 to 10 carbon atoms and may be for example as mononuclear group a phenyl, tolyl, xylyl, ethylphenyl, propylphenyl, isopropylphenyl, butylphenyl, isobutylphenyl, sec.-butylphenyl, tert.-butylphenyl or naphthyl group.

If the substituents $R_1$, $R_2$ or $R_3$ can also represent together with the C(R)-N< residue, or CH-N< residue respectively, a heterocyclic radical, it is preferably a 5-membered nitrogen-containing ring such as pyrrolidine in proline and 4-hydroxypyrrolidine in hydroxyproline, and pyroglutamic acid.

A heterocyclic residue as substituent of an optional substituted radical R, $R_1$, $R_2$ and $R_3$ may be a mono- or bicyclic, a monoaza or diazacyclic radical of aromatic character such as imidazolyl, as for example 4-imidazolyl, or indolyl, as for example 3-indolyl radical.

Moreover in addition when R or $R_1$ or the substituent of a lower alkyl group thereof is a heterocyclic ring containing one or more oxygen, nitrogen or sulphur atoms this may be, for example, aziridine, oxetane, thiophene, furan, pyridine, azepine, isoxazole, thiazole, pyrimidine, diazepine, thiadiazol, triazol, triazine, or imidazole or indole as mentioned above.

When R or $R_1$ is a lower alkenyl group this may be a straight or branched chain alkenyl group with 2 to 6 carbon atoms, and may be, for example, an ethenyl, allyl, crotyl, methallyl, pentenyl or hexenyl group.

When R or $R_1$ represents a lower alkynyl group this may be straight or branched chain alkynyl group with 2 to 6 carbon atoms, and may be, for example, an ethynyl, propynyl, butynyl, pentynyl or hexynyl group.

When R and $R_1$ together form a polymethylene chain, comprising a residue of 2 to 7 carbon atoms, this may be for example -$(CH_2)_2$-, -$(CH_2)_3$-, -$(CH_2)_4$-, -$(CH_2)_5$-, -$(CH_2)_6$-, -$(CH_2)_7$-, -$(CH_2)_2CHCH_3(CH_2)_2$- or -$(CH_2)_2NH(CH_2)_2$-.

The term etherified hydroxy is preferably lower alkoxy, such as methoxy, ethoxy, n-propyloxy, isopropyloxy or n-butyloxy and etherified mercapto is preferably lower alkylthio as for example methylthio, ethylthio, propylthio or isopropylthio.

The compounds containing S-substituted dithio groups are symmetrical or unsymmetrical residues of a compound of formula I bound to the other residue of a compound of formula I by a S-S-bridge, i.e.

A—S—S—B wherein A and B are the same or different and each is a residue of a compound of formula I formed by the loss of a hydrogen atom from a carbon atom in one of the substituents R, $R_1$, $R_2$ or $R_3$.

Examples of such compounds are those having the formulae Ia and Ib

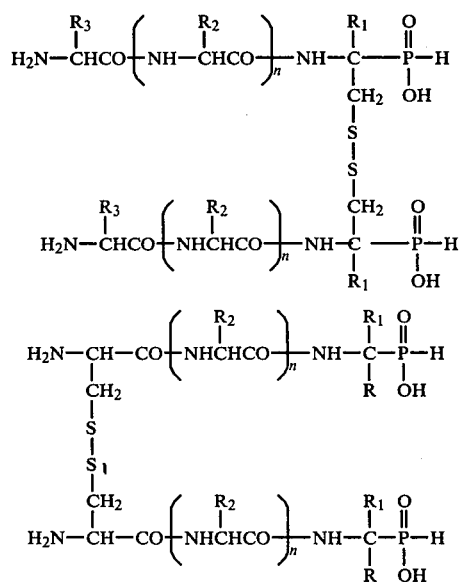

Functionally modified carboxy is, e.g. esterified carboxy, especially lower alkoxycarbonyl, also phenyl-lower-alkoxycarbonyl or carbamoyl.

When R, $R_1$, $R_2$ or $R_3$ is a group substituted by -$NR_4R_5$, in which one or both the $R_4$ and $R_5$ groups are lower alkyl, these groups may be lower alkyl groups as defined above. The -$NR_4R_5$ group including the different meanings enumerated above may be for example, methylamino, dimethylamino, methyl-ethylamino, ethylamino, diethylamino, propylamino, isopropylamino, dipropylamino or diisopropylamino.

The -$NR_4R_5$ groups in which $R_4$ and $R_5$ together form a polymethylene chain containing up to 6 carbon atoms which may optionally be interrupted by oxygen or nitrogen as for instance as substituent of R and $R_1$ and are preferably the morpholino or piperidino group.

Furthermore when R or $R_1$ is a group substituted by an aryloxy, the aryloxy group may be phenoxy, tolyloxy, xylyloxy, diiodo-hydroxy phenoxy.

The term halogen may be bromine or iodine but is preferably fluorine or chlorine.

Esters of the compounds of formula I are preferably those with low alkyl alcohols e.g. methanol, ethanol, n-propanol and n-butanol, aralkyl alcohols, e.g. benzyl alcohol and phenols e.g. phenol. Other alcohols which may be used to form the corresponding ester of the compound of formula I are alkanoyloxymethanols, e.g. acetoxymethanol or pivaloyloxymethanol; amino-lower-alkanoyloxymethanols e.g. α-amino-lower-alkanoyloxymethanols such as glycyloxy-methanol, L-valyloxymethanol or L-leucyloxymethanol; and also 3-hydroxyphthalide and 5-indanol.

Salts of the compounds of formula I and the esters are preferably addition salts of the following applicationally useful inorganic or organic acids or bases.

Examples of acids are hydrochloric, hydrobromic, sulphuric, phosphoric, methanesulphonic, ethanedisulphonic, acetic, trichloroacetic, oxalic, succinic, maleic, fumaric, malic, tartaric, citric and mandelic acids; examples of bases are Li-, Na-, K-, Ca-, Mg-, Al-, Fe-, $NH_4$- (and substituted ammonium) -hydroxides and -carbonates, as well as heterocyclic bases.

The new compounds of formula I can be applied to plants infected with bacteria or fungi and have low mammalian toxicity and low phytotoxicity. Another valuable property of the compounds is their synergistic antibacterial activity with other antimicrobial agents.

Particularly useful are compounds of formula I wherein R is hydrogen or deuterium, $R_1$ is hydrogen, deuterium or optitonally substituted lower alkyl, or $R_1$ represents, together with the >CR-N< residue to which it is attached, the atoms required to complete a 2-pyrrolidinyl group or homo-2-pyrrolidinyl group; $R_2$ and $R_3$ may be the same or different and each is hydrogen, optionally substituted lower alkyl, or aryl, and n is 0, 1, 2, or 3; as well as the esters and salts with alcohols, or acids or bases respectively; and all optical isomers thereof.

Preferred are compounds of formula I wherein R is hydrogen or deuterium, $R_1$ is methyl, $R_2$ and $R_3$ may be the same or different and each can be hydrogen, optionally substituted lower alkyl, or aryl and n is 0, 1, 2 or 3; as well as the esters and salts with alcohols, acids or bases, respectively; and all optical isomers thereof.

Especially valuable and suitable for said utility are compounds of formula I, wherein R is hydrogen; $R_1$ is methyl, $R_2$ and $R_3$ are hydrogen, or methyl and n is 0, 1, 2 or 3; and the esters and salts thereof with alcohols, acids or bases, respectively; and all optical isomers thereof.

Most preferred are compounds of formula I as listed in the following Examples.

The α-aminophosphonous acid peptide derivatives aforesaid i.e. the compounds of formula I and their salts can be prepared by methods usually known in the field of peptide chemistry; reference is made in this connection, e.g. to Schröder and Lübke, The Peptides, Volumes I and II (Academic Press; 1965), Lübke, Schröder and Kloos, "Chemie und Biochemie der Aminosäuren, Peptide and Proteine", Bände I und II (Georg Thieme Verlag, Stuttgart, 1974) and Weinsch "Synthese von Peptiden" (Synthesis of Peptides), Vol. XV/1 of Houben-Weyl, 'Methoden der organischen Chemie' (Methods of Organic Chemistry) (Georg Thieme Verlag, Stuttgart, 1974).

In order to understand readily the following described methods, α-amino acids of formula II

or peptide residues of formula III

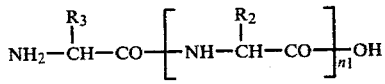

(III)

wherein $n_1$ can be 1, 2 or 3 corresponding to a fraction of formula I are simply referred to as α-amino acids.

The α-amino phosphonous acid of formula IV

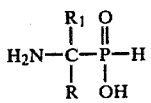

(IV)

or peptide residues of formula V

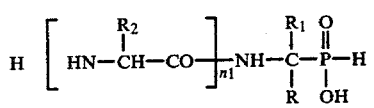

(V)

wherein $n_1$ can be 1, 2 or 3 corresponding to a fraction of formula I are simply referred to as α-amino phosphonous acids.

Compounds of formula IV wherein R and $R_1$ are each an alkyl group substituted by cycloalkyl; or wherein $R_1$ represents, together with the >C(R)-N< residue to which it is attached, the atoms required to form a heterocyclic radical are new compounds having valuable antimicrobial properties and, as such, form part of the present invention.

According to the present invention, there is also provided a process of producing a peptide derivative of formula I comprising reacting with an α-aminophosphonous acid, an activated, optionally N-protected α-amino acid of formula:

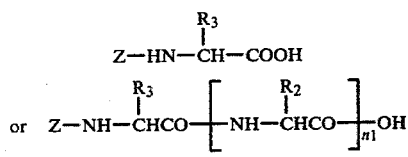

IIA

IIIA wherein $R_2$, $R_3$ and $n_1$ have their previous significance and Z is hydrogen or a protecting group.

The new compounds of formula I can thus be produced e.g. by the so-called anhydride method, by means of which an anhydride (optionally produced in situ) of an α-amino acid of formula IIIA or IIIA, is reacted with an α-amino phosphonous acid. The anhydride method is performed, in particular, using mixed anhydrides and also symmetrical anhydrides, e.g. anhydrides with inorganic acids, such as halides, especially acid chlorides (which can be obtained, e.g. by treatment of an α-amino acid with thionyl chloride, phosphorus pentachloride or oxalyl chloride; the so-called acid chloride method), azides (which can be obtained, e.g. from an ester of an α-amino acid by way of the corresponding hydrazide and treatment thereof with nitrous acid; the so-called azide method), anhydrides with carbonic acid semi-derivatives such as carbonic acid-lower-alkyl semi-esters (which can be obtained, e.g. by treatment of an α-amino acid with haloformic-acid-lower alkyl esters, such as chloroformic acid-lower-alkyl esters; this method is defined as the method of using mixed O-alkyl-carbonic acid anhydrides) or anhydrides with dihalogenated, particularly dichlorinated, phosphoric acid (which can be obtained, e.g. by treatment of an α-amino acid with phosphorus oxychloride; the phosphorus oxychloride method).

Furthermore it is also possible to use anhydrides with organic acids, such as mixed carboxylic acid anhydrides (which can be obtained, e.g. by treatment of an α-amino acid with phenylacetic acid chloride, pivalic acid chloride or trifluoroacetic acid chloride, this method is defined as the method using mixed carboxylic acid anhydrides), or symmetrical anhydrides (which can be obtained, e.g. by condensation of an α-amino acid of formula IIA or IIIA in the presence of a carbodiimide, such as N,N'-di-cyclohexylcarbodiimide or N-(3-dimethylaminopropyl)-N-ethyl-carbodiimide hydrochloride; this method is defined as the method using symmetrical anhydrides);

It is also possible to use internal anhydrides, for example by treatment of an α-amino acid of formula IIA or IIIA with phosgene, this method is the N-carboxylic anhydride method. Yet a further method for producing compounds of formula I is the azlactone method whereby e.g. the α-aminoacid is reacted with e.g. an anhydride to give an oxazolone which is further reacted with the α-aminophosphonous acid.

A further preferred method for producing compounds of formula I is the method of activated esters, whereby an activated ester (optionally formed in situ) of an α-amino acid of formula IIIA or IIIA is reacted with the amino group of an α-amino phosphonous acid. As activated esters are used, e.g. unsaturated esters at the linking carbon atom of the esterifying radical, e.g. compounds of the vinyl ester type, such as common vinyl esters (which can be obtained, e.g. by transesterification of an ester of an α-amino acid with vinyl acetate; activated vinyl ester method), carbamoylvinyl esters (which can be obtained, e.g. by treatment of α-amino acid with an isoxazolium reagent, e.g. 2-ethyl-5-phenyl-isoxazolium-3'-sulphonate; 1,2-oxazolium or Woodward method), or 1-lower-alkoxy-vinyl esters (which can be obtained, e.g. by treatment of an α-amino acid of formula IIA or IIIA with a lower alkoxyacetylene, e.g. ethoxyacetylene; this method is usually defined as ethoxyacetylene method).

It is also possible to use esters of the amidino type such as N,N'-disubstituted amidino esters (which can be obtained, e.g. by treatment of an α-amino acid, of formula IIA or IIIA which can be used as an acid addition salt, e.g. the hydrochloride, in combination with an α-amino phosphonous acid, which can be used also in the form of a salt, such as an ammonium salt, e.g. benzyltrimethylammonium salt, with a suitable, N,N'-disubstituted carbodiimide, e.g. N,N'-dicyclohexyl-carbodiimide; carbodiimide method) or N,N-di-substituted amidino esters (which can be obtained by treatment of an α-amino acid with an N,N-disubstituted cyanamide, e.g. N,N-diethylcyanamide, N,N-diphenylcyanamide or N,N-dibenzylcyanamide; the so-called cyanamide method).

Preferred activated esters are aryl esters (which can be obtained, e.g. by treatment of an α-amino acid of formula IIA or IIIA with a phenol suitably substituted by electron-withdrawing substituents, e.g. 4-nitrophenol, 3-methylsulphonylphenol, 2,4,5-trichlorophenol, 2,3,4,5,6-pentachlorophenol or 4-phenyldiazophenol, in the presence of a suitable condensation agent, such as 2-ethyl-5-phenyl-isoxazolium-3'-sulphonate; or by transesterification, e.g. by treatment of an α-amino acid of formula IIa or IIIA with an aryl ester suitable for transesterification, e.g. trifluoroacetic acid-4-nitrophenyl ester, if necessary in the presence of a suitable transesterification catalyst, e.g. pyridine; this method is defined as activated aryl ester method).

Further preferred activated esters are, inter alia, cyanomethyl esters (which can be obtained, e.g. by treatment of an α-amino acid of formula IIa or IIIA with chloroacetonitrile in the presence of a base; cyanomethyl ester method), thioesters (which can be obtained, e.g. by treatment of an α-amino acid of formula IIA or IIIA with thiophenols optionally substituted, e.g. by nitro, inter alia with use of the 1,2-oxazolium method or Woodward method; activated thiol ester method), or amino esters (which can be obtained, e.g. by treatment of an α-amino acid of formula IIa or IIIa with an N-hydroxy compound, e.g. N-hydroxy-piperidine, N-hydroxy-phthalimide, 8-hydroxyquinoline or 1-carboxy-2-hydroxy-1,2-dihydro-quinoline, and, especially, N-hydroxy-succinimide e.g. by the 1,2-oxazolium or Woodward method; this method is defined as activated N-hydroxy ester method).

Furthermore compounds of the formula I can be produced by the method using cyclic amides, particularly by reacting amides of α-amino acids of formula IIA or IIIA with five-membered diazacycles of aromatic character, such as corresponding imidazolides (which can be obtained, e.g. by treatment of the acid with N,N'-carbonyldiimidazole; imidazolide method), or pyrazolides (which can be obtained, e.g. by way of the acid hydrazide by treatment with acetylacetone; pyrazolide method), with an α-amino phosphonous acid to be joined.

In connection with the production of compounds of the formula I wherein the reaction of an α-amino acid of formula IIA or IIIA starting material with an α-amino phosphonous acid to be joined, can also be performed in stages. That is to say, the α-amino acid radicals forming a peptide radical can also be introduced individually or in the form of shorter peptide residues by the abovedescribed method, e.g. by reacting an α-amino acid compound, or a reactive derivative thereof, with an α-amino acid compound, or a derivative thereof, to be joined, or with a smaller peptide compound, or with a derivative thereof, corresponding to a fraction of a compound of formula I and reacting an amide compound thus obtainable, or a reactive derivative thereof, with a further α-amino phosphonous acid, or a derivative thereof, corresponding to a fraction of a compound of formula I.

As mentioned, the reaction of an α-amino acid or of a reactive derivative thereof, with an α-amino phosphonous acid or with a derivative thereof is performed in a manner known per se, with the reaction being carried out, if necessary or desired, in the presence of a suitable condensation agent, such as a corresponding basic agent, e.g. an organic base such as a tri-lower-alkylamine, e.g. triethylamine or diisopropyl-ethylamine, or an aromatic or heterocyclic base, e.g. pyridine, or a mixture of basic agents, usually in the presence of a suitable anhydrous solvent or solvent mixture and, if necessary, with cooling or heating, e.g. in a temperature range of about 0° C. to about 120° C., also, if necessary, in a closed vessel (optionally under pressure and/or in an inert gas atmosphere, e.g. in a nitrogen atmosphere).

According to the synthesis described before, compounds may be obtained in a form as described by formula I or in a form as described by formula VI

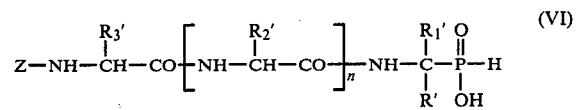

wherein $R'$, $R'_1$, $R'_2$ and $R'_3$ have the meanings as defined under formula I for the substituents $R$, $R_1$, $R_2$ and $R_3$ respectively, except that any amino group, hydroxy group or any other functional group which may be present, is in protected form where required, Z is hydrogen or a protecting group as usually used for an amino group, and n has the significance given under formula I.

Compounds of formula I and their salts may be obtained by cleaving off by methods known per se the protecting group(s) present in a compound of formula VI obtained by synthesis as described before.

The amino group or amino groups which may be present in $R'$, $R'_1$, $R'_2$ or $R'_3$ in formula VI can be protected with any amino-protecting group which is well-known in peptide chemistry, as for example mentioned in Lübke, Schröter and Kloos, "Chemie und Biochemie der Aminosäuren, Peptide und Proteine", Bd. I and II, (GeorgThieme Verlag Stuttgart, 1974).

Especially suitable amino-protecting groups for the purpose of the present invention are optionally substituted hydrocarbyloxycarbonyl groups e.g. aralkoxycarbonyl groups, particularly the benzyloxycarbonyl group, the tert.-butoxycarbonyl group, tert.-amyloxycarbonyl group, 2,2.2-trichlorethoxycarbonyl, 2-iodoethoxycarbonyl, adamantyl-(1)-oxycarbonyl group, [2-biphenyl-(4)-propyl-(2)]-oxycarbonyl group, piperidinooxycarbonyl group or furfuryloxycarbonyl group.

The amino-protecting group may also be of the so-called acyltype, i.e. optionally substituted alkanoyl, alkanesulphonyl and phosphoryl groups, as for example the carboxylic acid amide type, especially formyl, acetoacetyl, trifluoracetyl, phthalyl or 2-nitro-phenoxyacetyl or of the amide type of an inorganic acid, as for example toluene-sulphonyl, 2-nitrophenylsulphonyl or O,O-dibenzylphosphoryl.

Furthermore, the amono groups may be protected by hydrocarbyl groups, viz. optionally substituted aralkyl-protecting groups, as for example benzyl, dibenzyl or triphenylmethyl(trityl) group, or by protecting groups of the arylidene/enamine-type, as for example 2-hydroxy-5-chlorobenzylidene, 1-benzoyl-propenyl or 5,5-dimethyl-3-oxocyclohexenyl group.

Any carboxy or hydroxy group which may be present in $R'$, $R'_1$, $R'_2$ or $R'_3$ in compounds of formula VI can be protected by a conventional carboxy-protecting or hydroxy-protecting group respectively. For example, a carboxy group may be protected by conversion into ester, e.g. an alkyl ester, (e.g. a tert.-butyl ester) or an aralkyl ester (e.g. benzyl ester). Again, for example, a hydroxy group may be protected for example, by means of an aralkoxycarbonyl group (e.g. benzyloxycarbonyl), an alkanoyl group (e.g. acetyl, propionyl etc.), aroyl group (e.g. benzoyl), an alkyl group (e.g. tert.-butyl) or an aralkyl group (e.g. benzyl). The protection of other functional groups present in $R'$, $R'_1$, $R'_2$, or $R'_3$ may be carried out in a manner known per se.

A guanidino group may be protected by a nitro group or by groups mentioned for the amino group above, as for example an aryloxycarbonyl, especially benzyloxycarbonyl, furthermore tert.-butoxycarbonyl or adamantyl-(1)-oxy carbonyl group.

In an analogous manner an imidazole function (the nitrogen atom of the cyclic ring which may be substituted) may be protected by a benzyl group or a protecting group mentioned for a guanidino group with the exception of a nitro group.

A mercapto group may be protected as thioether, acylamidomethyl-thioether, thioacetal, thioester or disulfide, and following protecting groups, as for example the benzyl, 4-nitrobenzyl, 4-methoxybenzyl, triphenylmethyl(trityl), diphenylmethyl, 2-biphenyl-(4)-propyl-(2), tert.-butyl, acetylamino-methyl, 2,2,2-trifluor-1-tert.-butylcarbonyl-amino-ethyl, benzylmercaptomethyl, isobutoxymethyl, tetrahydro-pyranyl-(2), benzoyl, benzyloxycarbonyl, ethyl-aminocarbonyl, ethylmercapto or tert.-butylmercapto group may be used.

The protecting group Z may be any of the amino-protecting groups mentioned earlier in connection with R', R'$_1$, R'$_2$ and R'$_3$ or mentioned in "Lübke, Schroöder and Kloos, Chemie and Biochemie der Aminosäuren, Peptide und Proteine," Bd. I and II, (Georg Thieme Verlag Stuttgart, 1974).

The cleavage of the protecting group or protecting groups present in a compound of formula VI is carried out in accordance with methods known per se; that is to say, methods in actual use for or described in the literature especially described above on the cleavage of protecting groups. Thus, for example, an aralkoxycarbonyl group (e.g. benzyloxycarbonyl) or a tert.-butoxycarbonyl group may be cleaved off by hydrolysis (e.g. treatment with a mixture of hydrogen bromide and glacial acetic acid). The tert.-butoxycarbonyl group may also be cleaved off by means of hydrogen chloride in dioxan. A lower alkoxy group may be converted into a hydroxy group by treatment with a mixture of hydrogen bromide in glacial acetic acid or by means of trimethylchlorosilane followed by aqueous hydrolysis. The nitro group of an guanidino may be removed by hydrogenation with the help of catalyst. It will be appreciated that the cleavage of the protecting groups can be carried out in a single or in more than one step depending on the nature of the protecting groups present.

The starting materials, e.g. the α-amino acids of formulae II and III are known and can be produced in a manner known per se, optionally in situ. It is thus possible to use, e.g. an α-amino acid in the form of an acid addition salt, such as a hydrohalide, e.g. hydrochloride, and to liberate therefrom in the presence of a suitable basic agent, e.g. an inorganic metal base or an organic base, such as a suitable amine, e.g. tri-lower-alkylamine such as triethylamine or diiospropylethylamine, the free amine compound thereof. All of the α-amino phosphonous acids of formula IV (other than wherein R and R$_1$ are H) are new and described in copending British Pat. No. 21000/76. Starting materials hereinbefore.

Mixtures of racemic mixtures can be separated into the pure racemates on the basis of the physico-chemical differences of the constituents, in a known manner, for example by chromatography and/or fractional crystallisation.

Pure racemates can be resolved into the enantiomers according to known methods, for example by re-crystallisation from an optically active solvent, with the aid of microorganisms or by reaction with an optically active acid or base which forms salts with the racemic compound and separation of the salts obtained in this manner, for example on the basis of their different solubilities, and from the diastereomers the antipodes can be liberated by the action of suitable agents. Particularly customary optically active acids are, for example, the D- and L-forms of tartaric acid, di-o-toluyl-tartaric acid, malic acid, mandelic acid, camphor-10-sulphonic or quinine acid.

Particularly customary optionally active bases are, for example, D- and L-forms of α-methylbenzylamine, brucine, ephedrine and cinchonine. Resulting salts may be converted into other salts or into the free and optionally active acids or bases, and an optically active acid or base may be converted into an acid or base addition salt by the methods referred to above.

Diastereomeric mixtures can be separated into the individual diastereomers on the basis of the physico-chemical differences of the constituents, in known manner, e.g. by chromatography and/or fractional crystallisation for instance using an appropriate salt. A particularly useful salt is that formed from (+) α-methylbenzylamine, and the fractional crystallisation is conveniently effected in an organic solvent e.g. an alcohol or ether or mixtures thereof.

When R or R$_1$ is deuterium, this may be introduced additionally by deuteration of a compound of formula I where R or R$_1$ is hydrogen by procedures known to those skilled in the art.

The invention also provides a composition comprising an antimicrobially effective proportion of a compound of formula I and a solid carrier or liquid diluent.

The compounds of the formula I possess for practical purposes a very advantageous microbicidal spectrum for protecting cultivated plants. Examples of cultivated plants within the scope of this invention are: cereals, maize, rice. vegetables, sugar-beet, soya, ground nuts, fruit trees, ornamentals, vines, hops, cucumber plants (cucumber, marrows, melons), solanaceae, such as potatoes, tobacco plants and tomatoes, and also banana, cocoa and natural rubber plants.

With the active compounds of the formula I it is possible to inhibit or destroy the fungi which occur in plants or parts of plants (fruit, blossoms, leaves, stems, tubers, roots) in these and also related crops of useful plants, and also to protect from attack by such fungi the parts of plants which grow later. The active compounds are effective against the phytopathogenic fungi which belong to the following classes:

Ascomycetes (e.g. Helminthosporium); Basidiomycetes, in particular rust fungi (e.g. Puccinia); fungi imperfecti (e.g. Moniliales e.g. Cercospora); and against the Oomycetes belonging to the class of the Phycomycetes, such as Phytophthora. The compounds of the formula I are also effective against phytopathogenic bacteria such as Xanthomonas sp., Pseudomonas sp., Erwinia and Corynebacterium. In addition, the compounds of the formula I possess a systemic action. They can also be used as seed dressing agents for protecting seeds (fruit, tubers, grains) and plant cuttings from infection and from phytopathogenic microorganisms which occur in the soil.

The compounds of the invention also exhibit other valuable antimicrobial properties, for example, they are effective at low concentrations 0.001 to 50 μg/ml) in inhibiting the growth in vitro of pathogenic bacteria, as for example Eschericia coli, Proteus vulgaris, Proteus rettgeri, Salmonella typhimurium and other Enterobacteria, Pseudomonas aeruginosa and yeasts, as for example, Candida albicans and Candida tropicalis. The growth of both gram-negative bacteria and yeasts is inhibited, and is illustrated in Table I.

Table I

| Compound | Antimicrobial Activity Minimum Inhibitory Concentration μg/ml* | | | | | |
|---|---|---|---|---|---|---|
| | A | B | C | D | E | F |
| $\underset{H_2NCHCONHCHPO_2H_2}{\overset{CH_3 \quad\quad CH_3}{\| \quad\quad\quad \|}}$ | 0.01–0.2 | 0.1 | 0.2 | 0.1 | 8 | 1 |
| $H\left[\underset{\text{HNCHCO}}{\overset{L}{\underset{\|}{\overset{CH_3}{\|}}}}\right]_2 \underset{\text{NHCHPO}_2H_2}{\overset{R}{\underset{\|}{\overset{CH_3}{\|}}}}$ | 0.25–16 | 0.25 | 128 | 0.12 | >128 | — |
| $\underset{H_2NCHCONHCHPO_2H_2}{\overset{CH_3 \diagdown \quad \diagup CH_3}{\underset{\overset{\|}{CH} \quad\quad \overset{\|}{CH_3}}{}}}$ | 0.001–1 | 0.1 | 2 | 0.1 | 16 | 32 |
| $H\left[\underset{\text{HNCHCO}}{\overset{L}{\underset{\|}{\overset{CH_3}{\|}}}}\right]_4 \underset{\text{NHCHPO}_2H_2}{\overset{RS}{\underset{\|}{\overset{CH_3}{\|}}}}$ | 0.2–8 | 0.2 | 8 | 1 | 32 | 16 |

*Determined in a minimal agar
A = *Escherichia coli*;
B = *Salmonella typhimurium*;
C = *Proteus vulgaris*;
D = *Proteus rettgeri*;
E = *Pseudomonas Aeruginosa* ATCC 12055;
F = *Candida Albicans*.

The present invention still further provides an antimicrobial composition comprising an amount of a compound of formula I which is effective against the growth of bacterial and fungi which are pathogenic to plants.

The antimicrobial compositions according to the invention are prepared in a manner which is in itself known by intimate mixing and grinding of active compounds of the formula I with suitable carriers, if desired with addition of dispersing agents or solvents which are inert towards the active compounds. The active compounds may exist, and be used, in the following processing forms:

Solid processing forms: dusting agents, sprinkling agents, granules, coated granules, impregnated granules and homogeneous granules;
Active compound concentrates which are dispersible in water: wettable powders, pastes and emulsions:
Liquid processing forms: solutions.

In order to prepare solid processing forms (dusting agents, sprinkling agents and granules), the active compounds are mixed with solid carriers. Examples of carriers which can be used are kaolin, talc, bolus, loess, chalk, limestone, lime grits, attapulgite, dolomite, diatomaceous earth, precipitated silica, alkaline earth metal silicates, sodium and potassium aluminosilicates (feldspars and micas), calcium and magnesium sulphates, magnesium oxide, ground plastics, fertilisers, such as ammonium sulphate, ammonium phosphate, ammonium nitrate and urea, ground vegetable products, such as cereal flour, bark flour, wood flour, nutshell flour, cellulose powder, plant extract residues, active charcoal and the like, in each case on their own or as mixtures with one another.

Granules can be prepared by, for example, dissolving the active compounds in an organic solvent, applying the solution thus obtained to a granulated material, for example attapulgite, silica, granicalcium or bentonite, and then again evaporating the organic solvent.

It is also possible to prepare polymer granules by, for example, impregnating finished, porous polymer granules such as urea/formaldehyde polymers, polyacrylonitrile and polyesters, having a specific surface area and an advantageous predetermined absorption/desorption ratio, with the active compounds, for example in the form of their solutions (in a low-boiling solvent) and removing the solvent. Such polymer granules can be applied in the form of micro-granules with bulk densities of, preferably, 300 g/liter to 600 g/liter, also with the aid of atomisers. Atomising can be effected over extensive treatment areas by means of aircraft.

Granules can also be obtained by compacting the carrier with the active compounds and additives and then comminuting the mixture.

Furthermore, it is possible to add to these agents additives which stabilise the active compound and/or nonionic, anionic and cationic materials which, for example, improve the adhesion of the active compounds to plants and parts of plants (adhesives and glues) and/or ensure better wettability (wetting agents) and dispersibility (dispersing agents). It is possible to use, for example, the following materials as adhesives: olein/lime mixture, cellulose derivatives (methylcellulose and carboxymethylcellulose), hydroxyethylene glycol ethers of monoalkylphenols and dialkylphenols having 5 to 15 ethylene oxide residues per molecule and 8 to 9 carbon atoms in the alkyl radical, ligninsulphonic acid, its alkali metal salts and alkaline earth metal salts, polyethylene glycol ethers ("Carbowaxes"), fatty alcohol polyglycol ethers having 5 to 20 ethylene oxide residues per molecule and 8 to 18 carbon atoms in the fatty alcohol part, condensation products of ethylene oxide and propylene oxide, polyvinylpyrrolidones, polyvinyl alcohols, condensation products of urea/formaldehyde and latex products.

Water-dispersible active compound concentrates, i.e. wettable powders, pastes and emulsion concentrates, are agents which can be diluted with water to any desired concentration. They consist of active compound, carrier, if desired additives which stabilise the active compound, surface-active substances and anti-foaming agents and, if desired, solvents.

The wettable powders and pastes are obtained by mixing and grinding the active compounds with dispersing agents and pulverulent carriers in suitable devices until homogeneity is achieved. Examples of carriers are those mentioned above for the solid processing forms. In some cases it is advantageous to use mixtures of different carriers. Examples of dispersing agents which can be used are: condensation products of sulphonated naphthalene and sulphonated naphthalene derivatives with formaldehyde, condensation products of naphthalene or of naphthalenesulphonic acids with phenol and formaldehyde, and alkali metal salts, ammonium salts and alkaline earth metal salts of ligninsulphonic acid, as well a alkylarylsulphonates, alkali metal salts and alkaline earth metal salts of dibutylnaphthalenesulphonic acid, fatty alcohol sulphates, such as salts of sulphated hexadecanols and heptadecanols, and salts of sulphated fatty alcohol polyethylene glycol ethers, the sodium salt of oleyl methyl tauride, di-tertiary acetylene glycols, dialkyldilaurylammonium chloride and alkali metal salts and alkaline earth metal salts of fatty acids.

Examples of anti-foaming agents which can be used are silicones.

The active compounds are mixed, ground, sieved and strained with the above mentioned additives, in such a way that the particle size of the solid component does not exceed 0.02 to 0.04 mm in the case of wettable powders and 0.03 mm in the case of pastes. To prepare emulsion concentrates and pastes, dispersing agents, such as have been listed in the preceding sections, organic solvents and water are used. Examples of suitable solvents are the following: alcohols, benzene, xylenes, toluene, dimethylsulphoxide, N,N-dialkylated amides and trialkylamines. The solvents must be virtually odourless and inert towards the active compounds and should not be readily combustible.

Furthermore, the agents according to the invention can be used in the form of solutions. For this purpose, the active compound or several active compounds of the formula I is/are dissolved in suitable organic solvents, solvent mixtures, water or mixtures of organic solvents with water.

The content of active compound in the composition agents described above is between 0.1 and 95%, preferably between 1 and 80%.

Use forms can be diluted down to 0.001%. The amounts used are as a rule 0.1 to 10 kg of active substance/hectare, preferably 0.25 to 5 kg of active substance/hectare.

Some Examples will now begin, all parts and percentages being by weight unless otherwise stated. The temperatures are given in centigrade.

EXAMPLE 1

(a) RS-1-Aminoethanephosphonous acid (8.25 g, 0.075 M) was dissolved in water (375 ml) and ethanol (190 ml) and the solution was cooled to 10°. Sodium bicarbonate (A.R. grade, 12.75 g, 0.15 M) was added portionwise with stirring and the resulting solution was cooled to 0°. A solution of the N-hydroxysuccinimide ester of N-benzyloxycarbonyl-L-alanine (24 g, 0.075 M) in hot ethanol (260 ml) was added over a period of 10 minutes maintaining the internal temperature at 0°.

The heterogeneous mixture was stirred for 2 hours at 0° and then 24 hours at room temperature. The clear solution was evaporated at room temperature to give a white gummy solid. Treatment of this residue with cold dilute hydrochloric acid (2 N, 150 ml) gave a white powdery solid which was allowed to stand 2 hours at room temperature. The mixture was diluted with an equal volume of water and allowed to stand 24 hours at 0°. Filtration gave a mixture of the 1- (S) and 1-(R)-diastereomers of 1-[(N-benzyloxycarbonyl-L-alanyl)amino]-ethanephosphonous acid, 12.2 g, m.p. 175°-6°, $[\alpha]_D^{20} -45.7°$ (2% in glacial acetic acid).

(b) This mixture of diastereomers of 1-[(N-benzyloxycarbonyl-L-alanyl)amino]-ethanephosphonous acid (12 g) was added to a solution of hydrogen bromide in glacial acetic acid (50 ml, 45% w/w) at 0° and the mixture was stirred for thirty minutes. The solution was allowed to warm up to room temperature and then evaporated to an oily residue. This residue was dissolved in dry methanol (60 ml.) and propylene oxide was carefully added with cooling. The mixture was stirred for two hours at room temperature and allowed to crystallise at 0°. It gave a mixture of diastereomers of 1-(L-alanylamino)-ethanephosphonous acid [m.p. 276° decomp., $[\alpha]_D^{20} -75.6°$ (2% in water)].

EXAMPLE 2

The procedure described in Example 1a was repeated using 1R-1-aminoethanephosphonous acid instead of RS-1-aminoethanephosphonous acid to give 1R-1-[(N-benzyloxycarbonyl-L-alanyl)amino]-ethanephosphonous acid. m.p. 180°-2° decomp., $[\alpha]_D^{20} -60°$ (2% in glacial acetic acid). [The (+)-α-methylbenzylamine salt of this compound had m.p. 206°-7° decomp. and $[\alpha]_D^{20} -44.7°$ (2% in methanol)].

By the same procedure described in Example 1b, this compound was converted to 1R-1-(L-alanylamino)-ethanephosphonous acid. m.p. 276° decomp., $[\alpha]_D^{20} -80.1°$ (2% in water).

EXAMPLE 3

(a) 1S-1-Aminoethanephosphonous acid (3.4 g., 0.031 M) was dissolved in water (155 ml.) and ethanol (186 ml.) and the solution was cooled to 10°. Sodium bicarbonate (A.R. grade, 5.25 g., 0.062 M) was added portionwise with stirring and the resulting solution was cooled to 0°. A solution of N-hydroxysuccinimide ester of N-benzyloxycarbonyl-L-alanine (9.9 g., 0.031 M) in hot ethanol (44 ml.) was added over a period of 10 minutes maintaining the internal temperature of 0°. This mixture was stirred for 2 hours at 0° and 24 hours at room temperature. The clear solution was evaporated at room temperature to give a gummy solid. This material was stirred with ethanol (50 ml) and the insoluble material was removed by filtration. The filtrate was evaporated to dryness, redissolved in absolute ethanol and made just acid with a solution of hydrogen chloride in ethanol. The cloudy solution was diluted with ether (75 ml.) and a white solid was obtained which was dissolved in 75 ml. ethanol and clarified with filter-aid. Evaporation of the filtrate gave 1S-[(N-benzyloxycarbonyl-L-alanyl)amino]-ethanephosphonous acid m.p. 143°–5° decomp., $[\alpha]_D^{20} +33.8°$ (2% in glacial acetic acid. [The (+)-α-methylbenzylamine salt of this compound had m.p. 205°–6° decomp., and $[\alpha]_D^{20} +19.8°$ (2% in methanol)].

(b) By the same procedure described in Example 1b, this compound was converted to 1S-1-(L-alanylamino)-ethanephosphonous acid m.p. 274° decomp., $[\alpha]_D^{20} +115°$ (2% in water).

EXAMPLE 4

(a) The procedure described in Example 1a was repeated to give a mixture of the 1S- and 1R-diastereomers of 1-[(N-benzyloxycarbonyl-L-alanyl)amino]-ethanephosphonous acid m.p. 175°–6°, $[\alpha]_D^{20} -45.7°$ (2% in glacial acetic acid); (the filtration liquors from which it was obtained being set aside for use in Example 4b). This solid was converted to its (+)-α-methylbenzylamine salt in ethanol solvent and recrystallised from ethanol to constant melting point and constant specific rotation, identical to that described in Example 2a, namely, m.p. 206°–7° decomp., and $[\alpha]_D^{20} -44.7°$ (2% in methanol).

By the procedure described in Example 1b this salt was converted to 1R-1-(L-alanylamino)-ethanephosphonous acid m.p. 276° decomp., $[\alpha]_D^{20} -80.1°$ (2% in water).

(b) The filtration liquors obtained in Example 4a were evaporated to an oil which was dissolved in ethanol and the solid which formed was collected by filtration. The filtrate was evaporated to dryness and the oil so obtained was stirred with acetone. The waxy solid which formed was collected by filtration and the filtrate again evaporated to dryness. The resultant oil was dissolved in water, extracted successively with ether, propylene oxide, and finally petroleum ether. Evaporation of the aqueous portion gave an oil which on treatment with (+)-α-methylbenzylamine in isopropanol solvent gave the (+)-α-methylbenzylamine salt of 1S-1-[(N-benzyloxycarbonyl-L-alanyl)-amino]-ethanephosphonous acid m.p. 205°–6° decomp., $[\alpha]_D^{20} +19.5°$ (2% in methanol), identical to that described in Example 3a.

By the procedure described in Example 1b this salt was converted to 1S-1-(L-alanylamino)-ethanephosphonous acid m.p. 275° decomp., $[\alpha]_D^{20} +115°$ (2% in water) identical to that obtained in Example 3b.

EXAMPLE 5

(a) 1R-1-(L-alanylamino)-ethanephosphonous acid (1.8 g., 0.01 M) was dissolved in a mixture of water (50 ml.) and ethanol (25 ml) and the solution was cooled to 10°; sodium bicarbonate (A.R. grade 1.7 g, 0.02 M) was added portionwise and the solution was cooled to 0°. A solution of the N-hydroxysuccinimide ester of N-benzyloxycarbonyl-L-alanine (3.2 g, 0.01 M) in hot ethanol (35 ml) was added over a period of 10 minutes maintaining the internal temperature at 0°. The heterogeneous mixture was stirred for 2 hours at 0° and then 24 hours at room temperature. The resulting clear solution was evaporated at room temperature to give a white gummy solid. This residue was stirred with 25 ml of dilute hydrochloric acid (2 N) for 2 hours at room temperature and allowed to crystallise at 0°. Filtration gave 1R-1-[(N-benzyloxycarbonyl-L-alanyl)-L-alanylamino]-ethanephosphonous acid, m.p. 221°, $[\alpha]_D^{20} -73.6°$ (1% in glacial acetic acid).

(b) By the same procedure as described in Example 1b 1R-1-[(N-benzyloxycarbonyl-L-alanyl)-L-alanylamino]-ethanephosphonous acid was converted to 1R-1-(L-alanyl-L-alanylamino)-ethanephosphonous acid, m.p. 263°–264°, $[\alpha]_D^{20} -112.7°$ (1% in water).

EXAMPLE 6

The procedure described in Example 5a was repeated using 1R-1-(L-alanyl-L-alanylamino)-ethanephosphonous acid instead of 1R-1-(L-alanylamino)-ethanephosphonous acid to give 1R-1-[(N-benzyloxycarbonyl-L-alanyl)-L-alanyl-L-alanylamino]-ethanephosphonous acid, m.p. 242°, $[\alpha]_D^{20} -114.3°$ (1% in 2N.NaOH).

By the same procedure described in Example 1b, this compound was converted to 1R-1-(L-alanyl-L-alanyl-L-alanylamino)-ethanephosphonous acid, m.p. 266°–267°, $[\alpha]_D^{20} -136.3°$ (1% in water).

EXAMPLE 7

The procedure described in Example 5a was repeated using 1R-1-(L-alanyl-L-alanyl-L-alanylamino)-ethanephosphonous acid instead of 1R-1-(L-alanylamino)-ethanephosphonous acid to give 1R-1-[(N-benzyloxycarbonyl-L-alanyl)-L-alanyl-L-alanyl-L-alanylamino]-ethanephosphonous acid, m.p. 274°–275°, $[\alpha]_D^{20} -133°$ (0.4% in 2N.NaOH).

By the same procedure described in Example 1b, this compound was converted to 1R-1-(L-alanyl-L-alanyl-L-alanyl-L-alanylamino)-ethanephosphonous acid, m.p. 288°–289°, $[\alpha]_D^{20} -154.2°$ (0.6% in water).

EXAMPLE 8

(a) The procedure described in Example 1a was repeated using RS-1-amino-2-methylpropanephosphonous acid instead of DL-1-amino-ethanephosphonous acid to give a mixture of the 1R- and 1S-diastereomers of 1-[(N-benzyloxycarbonyl-L-alanyl)amino]-2-methylpropanephosphonous acid as a viscous pale yellow oil, $[\alpha]_D^{23} -17°$ (2% in ethanol).

(b) By the same procedure described in Example 1b, this product was converted to a mixture of the diastereomers of 1-(L-alanylamino)-2-methylpropanephosphonous acid, m.p. 260° (decomp.), $[\alpha]_D^{22} -40°$ (1% in water).

EXAMPLE 9

(a) The procedure described in Example 1a was repeated using [1-(−)]-1-amino-2-methylpropanephosphonous acid instead of RS-1-aminoethanephosphonous acid to give [1-(−)]-1-[(N-benzyloxycarbonyl-L-alanyl)-amino]-2-methylpropanephosphonous acid m.p. 174°–5°, $[\alpha]_D^{20} -70°$, (1% in glacial acetic acid). [The (+)-α-methylbenzylamine salt of this compound had m.p. 183°–5° and $[\alpha]_D^{20} -43.9°$ (2% in methanol).]

(b) By the same procedure as described in Example 1b, this compound was converted to [(1-(−)]-1-(L-alanylamino)-2-methylpropanephosphonous acid m.p. 271°–2° decomp., $[\alpha]_D^{20} -54.0°$ (1% in water).

EXAMPLE 10

(a) The procedure described in Example 3a was repeated using [1-(+)-1-amino-2-methylpropanephosphonous acid instead of [1-(S)]-1-aminoethanephosphonous acid to give [1-(+)]-1-[(N-benzyloxycarbonyl-L-alanyl)amino]-2-methyl-propanephosphonous acid as an oil.

[The (+)-α-methylbenzyl-amine salt of this compound had m.p. 184°-5° and $[\alpha]_D^{20}+15.7°$ (2% in methanol).]

(b) By the same procedure as described in Example 1b, this compound was converted to [1-(+)]-1-(L-alanylamino)-2-methylpropanephosphonous acid m.p. 263°-4° decomp. $[\alpha]_D^{20}+79.6°$ (1% in water).

EXAMPLE 11

The procedure described in Example 3a was repeated using RS-1-amino-3-carboisopropoxypropanephoshonous acid instead of 1S-1-aminoethanephosphonous acid to give 1RS-1-[(benzyloxycarbonyl-L-alanyl)amino]-3-carboisopropoxypropanephosphonous acid as an oil.

This compound was heated with aqueous hydrogen bromide for thirty minutes at 50°. The solution was evaporated and the residue was stirred with propylene oxide for 2 hours. The mixture was diluted with an equal volume of ethanol and filtered to give 1RS-1-(L-alanylamino)-3-carboxypropanephosphonous acid.

EXAMPLE 12

(a) The procedure described in Example 1a was repeated using the N-hydroxysuccinimide ester of N-benyloxycarbonyl-L-valine instead of the N-hydroxysuccinimide ester of N-benzyloxycarbonyl-L-alanine. A mixture of the 1R- and 1S-diastereomers of 1-[(N-benyloxycarbonyl-L-valyl)amino]-ethanephosphonous acid, m.p. 202°, $[\alpha]_D^{20}-38.5°$ (2% in glacial acetic acid) was obtained.

(b) By the same procedure as described in Example 1b this product was converted to a mixture of diastereomers of 1-(L-valylamino)ethanephosphonous acid, m.p.>260°, $[\alpha]_D^{25}-30°$ (1% in water).

EXAMPLE 13

The procedure described in Example 3a was repeated using the N-hydroxysuccinimido ester of N-benzyloxycarbonyl-L-phenylalanine instead of that of N-benyloxycarbonyl-L-alanine and 1RS-1-aminoethanephosphononous acid instead of 1S-1-aminoethanephosphonous acid to give 1RS-1-[(N-benyloxycarbonyl-L-phenylalanyl)amino]-ethanephonous acid, m.p. 157° C., $[\alpha]_D^{23}+6.5°$ (2% in glacial acetic acid).

By the same procedure described in Example 1b this compound was converted to 1RS-1-(L-phenylalanylamino)-ethanephosphonous acid.

EXAMPLE 14

The procedure described in Example 3a was repeated using the N-hydroxysuccinimide ester of α,ε-di-N-benzyloxycarbonyl-L-lysine instead of that of N-benzyloxycarbonyl-L-alanine and 1RS-aminoethanephoshonous acid instead of 1S-1-aminoethanephosphonous acid to give 1RS-1(α,ε-[di-N-benyloxycarbonyl-L-lysyl)amino]-ethanephosphonous acid, m.p. 145°-150° C., $[\alpha]_D^{23}-7°$ (2% in glacial acetic acid).

By the same procedure described in Example 1b, this compound was converted to 1RS-1-(L-lysylamino)-ethanephosphonous acid.

EXAMPLE 15

The procedure described in Example 3a was repeated using the N-hydroxysuccinimide ester of N-benzyloxycarbonyl-L-valine instead of that of N-benzyloxycarbonyl-L-alanine and RS-1-amino-3-methylthiopropanephosphonous acid instead of 1S-1-aminoethanephosphonous acid to give 1RS-1-[(N-benzyloxycarbonyl-L-valyl)amino]-3-methylthiopropanephosphonous acid, m.p. 154°-155° C.

By the same procedure described in Example 1b, this compound was converted to 1RS-1-(L-valylamino)-3-methylthiopropanephosphonous acid.

EXAMPLE 16

The procedure described in Example 3a was repeated using the N-hydroxysuccinimide ester of N-benzyloxycarbonyl-L-methionine instead of that of N-benzyloxycarbonyl-L-alanine and RS-1-amino-2-methylpropanephosphonous acid instead of 1S-1-aminoethanephosphonous acid to give 1RS-1-[(N-benzyloxycarbonyl-L-methionyl)amino]-2-methylpropanephosphonous acid, m.p. 159°-162° C., $[\alpha]_D^{20}-12.5°$ (2% in glacial acetic acid).

By the same procedure described in Example 1b, this compound was converted to 1RS-1-(L-methionylamino)-2-methylpropanephosphonous acid, m.p. 258° C., $[\alpha]_D^{22}-24°$ (1% in water).

EXAMPLE 17

(a) 5-hydroxypentanal (4.1 g.) was added to a suspension of benzhydrylammonium hypophosphite (10.0 g.) in boiling dioxan (50 ml.) during 1 hour while removing some dioxan (30 ml.) via a Dean & Stark apparatus. The residue was cooled and diluted with ethanol. There was obtained DL-1-N-benzhydrylamino-5-hydroxypentanephosphonous acid m.p. 184°. RS-1-N-benzyhydrylamino-5-hydroxypentanephosphonous acid (3.3 g.) was stirred at 80° with aqueous hydrogen bromide (60%) (20 ml.) for 2 hours and was then refluxed for a further 2 hours. The mixture was cooled and extracted with ether and the aqueous phase was evaporated to dryness. The residue was then dissolved in absolute alcohol and propylene oxide was added until crystallisation started and the mixture was allowed to stand for 12 hours. It gave RS-1-amino-5-bromopentanephosphonous acid (1.4 g. m.p. 174° decomp.)

This compound (1.25 g.) was refluxed with aqueous ammonia (9 ml., 50%) for five hours. The mixture was evaporated to dryness and ammonium bromide was removed by filtration after precipitation using ethanol and ether. The filtrate was evaporated to dryness and the residual oil was dissolved in methanol. A large volume of propylene oxide was added to precipitate RS-piperidine-2-phosphonous acid (m.p. 255°-8° decomp.).

(b) The procedure described in Example 3a was repeated using RS-piperidine-2-phosphonous acid instead of 1S-1-aminoethanephosphonous acid to give 2RS-N-(N-benzyloxycarbonyl-L-alanyl)-piperidine-2-phosphonous acid.

By the same procedure as described in Example 1b, this compound was converted to 2RS-N-(L-alanyl)-piperidine-2-phosphonous acid.

EXAMPLE 18

(a) The procedure described in Example 19a was repeated using 4-hydroxybutanal instead of 5-hydroxypentanal to give RS-pyrrolidine-2-phosphonous acid.

(b) The procedure described in Example 1a was repeated using RS-pyrrolidine-2-phosphonous acid instead of RS-1-aminoethanephosphonous acid to give 2RS-N-(N-benzyloxycarbonyl-L-alanyl)-pyrrolidine-2-phosphonous acid.

By the same procedure as described in Example 1b, this compound was converted to 2RS-N-(L-alanyl)-pyrrolidine-2-phosphonous acid.

EXAMPLE 19

(a) The procedure described in Example 1a was repeated using the N-hydroxysuccinimide ester of N-benzyloxycarbonyl-D-alanine instead of the N-hydroxysuccinimide ester of N-benzyloxycarbonyl-L-alanine. A mixture of the 1R and 1S-diastereomers of 1-[(N-benzyloxycarbonyl-D-alanyl)amino]-ethanephosphonous acid, m.p. 175°–176°, $[\alpha]_D^{22} + 51.5°$ (2% in glacial acetic acid) was obtained.

(b) By the same procedure described in Example 1b this product was converted to a mixture of diastereomers of 1-(D-alanylamino)-ethanephosphonous acid, m.p. >260°, $[\alpha]_D^{24} + 65.5°$ (2% in water).

EXAMPLE 20

(a) The procedure described in Example 1a was repeated using the N-hydroxysuccinimide ester of N-benzyloxycarbonylglycine instead of the N-hydroxysuccinimide ester of N-benzyloxycarbonyl-L-alanine. A mixture of the 1S- and 1R-enantiomers of 1-(N-benzyloxycarbonylglycyl)-aminoethanephosphonous acid, m.p. 86°–87° was obtained.

(b) By the same procedure described in Example 1b this product was converted to the racemate of 1-glycylaminoethanephosphonous acid, m.p. 254°–255°.

EXAMPLE 21

(a) The procedure described in Example 1a was repeated using the N-hydroxy-succinimide ester of N-benzoyloxycarbonyl-3-fluoro-D-alanine to give a mixture of the 1R- and 1S-diastereomers of 1-(N-benzyloxycarbonyl-3-fluoro-D-alanyl)amino-ethanephosphonous acid.

(b) By the same procedure described in Example 1b this product was converted to a mixture of the diastereomers of 1-(3-fluoro-D-alanylamino)-ethane-phosphonous acid.

EXAMPLE 22

1RS-1-(L-Alanylamino-ethanephosphonous acid (1.8014 g, 0.01 M) was dissolved in a solution of cold water (10 ml) and sodium hydroxide (0.40 g., 0.01 M) and the mixture was stirred for five minutes. The mixture was evaporated to dryness, stirred with absolute ethanol, and filtered to give the sodium salt of 1RS-1-(L-alanylamino)-ethanephosphonous acid.

EXAMPLE 23

1RS-1-(L-Alanylamino)-ethanephosphonous acid (1 g.) was dissolved in a solution of absolute ethanol saturated with dry hydrogen chloride (50 ml). The mixture was evaporated to dryness to give the hydrochloride of 1RS-1-(L-alanylamino)-ethanephosphonous acid.

EXAMPLE 24

(a) The procedure described in Example 1a was repeated using the N-hydroxysuccinimide ester of N-benzyloxycarbonyl-DL-alanine instead of the N-hydroxysuccinimide ester of N-benzyloxycarbonyl-L-alanine to give a mixture of the 1-(+)- and the 1-(−)-diastereomers of 1-[(N-benzyloxycarbonyl-D-alanyl)amino]-ethanephosphonous acid and the 1-(+)- and the 1-(−)-diastereomers of 1-[(N-benzyloxycarbonyl-L-alanyl)amino]-ethanephosphonous acid.

(b) By the same procedure described in Example 1b this product was converted to a mixture of the diastereomers of 1-(D-alanylamino)-ethanephosphonous acid and the diastereomers of 1-(L-alanylamino)-ethanephosphonous acid.

EXAMPLE 25

(a) The procedure described in Example 1a was repeated using aminomethanephosphonous acid instead of DL-1-aminoethanephosphonous acid to give (N-benzyloxycarbonyl-L-alanyl)aminomethanephosphonous acid.

(b) By the same procedure described in Example 1b this product was converted to L-alanylaminomethanephosphonous acid.

EXAMPLE 26

The procedure described in Example 1a was repeated using the N-hydroxysuccinimide ester of L-pyroglutamic acid instead of the N-hydroxysuccinimide ester of N-benzyloxycarbonyl-L-alanine to give a mixture of the 1-(+)- and 1-(−)-diastereomers of 1-(L-pyroglutamylamino)-ethanephosphonous acid.

EXAMPLE 27

(a) By the procedure described in Example 1a using instead of the N-hydroxysuccinimide ester of N-benzyloxycarbonyl-L-alanine, N-hydroxysuccinimide esters of the following N-protected derivatives of L-alanine:

N-p-nitrobenzyloxycarbonyl
N-p-chlorobenzyloxycarbonyl
N-t-butoxycarbonyl
N-cyclopentyloxycarbonyl
N-2-(p-xenyl)isopropoxycarbonyl
N-furfuryloxycarbonyl
N-p-decyloxybenzyloxycarbonyl
N-ethoxycarbonyl
N-n-butyloxycarbonyl
N-butyloxycarbonyl
N-isobutyloxycarbonyl
N-1-methylheptyloxycarbonyl
N-octadecenyloxycarbonyl
N-formyl
N-trifluoroacetyl
N-propionyl were obtained the 1-(+)- and the 1-(−)-diastereomeric mixture of the following products respectively:

1-[(N-p-nitrobenzyloxycarbonyl-L-alanyl)amino]-ethanephosphonous acid
1-[(N-p-chlorobenzyloxycarbonyl-L-alanyl)amino]-ethanephosphonous acid
1-[(N-t-butoxycarbonyl-L-alanyl)amino]-ethanephosphonous acid
1-[(N-cyclopentyloxycarbonyl-L-alanyl)amino]-ethanephosphonous acid
1-[N-2-(p-xenyl)isopropoxycarbonyl-L-alanyl)amino]-ethanephosphonous acid
1-[(N-furfuryloxycarbonyl-L-alanyl)amino]-ethanephosphonous acid
1-[(N-p-decyloxybenzyloxycarbonyl-L-alanyl)amino]-ethanephosphonous acid
1-[(N-ethoxycarbonyl-L-alanyl)amino]-ethanephosphonous acid
1-[(N-isopropoxycarbonyl-L-alanyl)amino]-ethanephosphonous acid
1-[(N-n-butyloxycarbonyl-L-alanyl)amino]-ethanephosphonous acid
1-[(N-isobutyloxycarbonyl-L-alanyl)amino]-ethanephosphonous acid 1-[(N-1-methylheptyloxycarbonyl-L-alanyl)amino]-ethanephosphonous acid
1-[(N-octadecenyloxycarbonyl-L-alanyl)amino]-ethanephosphonous acid
1-[(N-formyl-L-alanyl)amino]-ethanephosphonous acid
1-[(N-trifluoroacetyl-L-alanyl)amino]-ethanephosphonous acid
1-[(N-propionyl-L-alanyl)amino]-ethanephosphonous acid (b) These products were converted by known literature methods to a mixture of the diastereomers of 1-(L-alanylamino)-ethanephosphonous acid.

EXAMPLE 28

By the procedure described in Example 1a using instead of the N-hydroxysuccinimide ester of N-benzyloxycarbonyl-L-alanine, the N-hydroxysuccinimide esters of the following N-protected derivatives of glycine:

N-p-bromobenzyloxycarbonyl
N-p-methoxybenzyloxycarbonyl
N-t-amyloxycarbonyl
N-cyclohexyloxycarbonyl
N-l-menthyloxycarbonyl
N-$\beta,\beta,\beta$-trichloroethoxycarbonyl
N-allyloxycarbonyl
N-n-propoxycarbonyl
N-sec-butoxycarbonyl
N-2-ethylhexyloxycarbonyl
N-decyloxycarbonyl
N-octadecyloxycarbonyl
N-4-t-butylcyclohexyloxycarbonyl
N-phenoxycarbonyl
N-piperidinoxycarbonyl
N-phthalyl
N-acetyl
N-p-toluenesulphonyl were obtained the 1-(+)- and 1-(−)-enantiomeric mixtures of the following products respectively:

1-[(N-p-bromobenzyloxycarbonylglycyl)]aminoethanephosphonous acid
1-[(N-p-methoxybenzyloxycarbonylglycyl)]aminoethanephosphonous acid
1-[(N-t-amyloxycarbonylglycyl)]aminoethanephosphonous acid
1-[(N-cyclohexyloxycarbonylglycyl)]aminoethanephosphonous acid
1-[(N-l-menthyloxycarbonylglycyl)]aminoethanephosphonous acid
1-[(N-$\beta,\beta,\beta$-trichloroethoxycarbonylglycyl)]aminoethanephosphonous acid
1-[(N-allyloxycarbonylglycyl)]aminoethanephosphonous acid
1-[(N-n-propoxycarbonylglycyl)]aminoethanephosphonous acid
1-[(N-sec-butoxycarbonylglycyl)]aminoethanephosphonous acid
1-[(N-2-ethylhexyloxycarbonylglycyl)]aminoethanephosphonous acid
1-[(N-decyloxycarbonylglycyl)]aminoethanephosphonous acid
1-[(N-octadecyloxycarbonylglycyl)]aminoethanephosphonous acid
1-[(N-4-t-butylcyclohexyloxycarbonylglycyl)]aminoethanephosphonous acid
1-[(N-phenoxycarbonylglycyl)]aminoethanephosphonous acid
1-[(N-piperidinoxycarbonylglycyl)]aminoethanephosphonous acid
1-[(N-phthalylglycyl)]aminoethanephosphonous acid
1-[(N-acetylglycyl)]aminoethanephosphonous acid
1-[(N-p-toluenesulphonylglycyl)]aminoethanephosphonous acid (b) These products were converted by known literature methods to the racemate of 1-glycylaminoethanephosphonous acid.

EXAMPLE 29

Activity against Puccinia graminis on wheat (a) Residual-protective activity

Six day old wheat plants were sprayed with a broth containing 0.06% of the compound to be tested. After 24 hours the treated plants were infected with a suspension of fungal uredo spores. The plants were then incubated for 48 hours at ca. 20° C. and a relative humidity of 95–100% and placed in a greenhouse at ca. 22° C.

Evaluation of the development of Rustpustules took place 12 days after infection.

(b) Systemic activity

Five day old wheat plants were watered with a broth containing the test compound to give a concentration thereof of 0.0006% with respect to soil volume. Care was taken to prevent contact between the broth and the aerial plant parts. After 48 hours the treated plants were infected with a suspension of fungal uredospores.

The plants were then incubated for 48 hours at ca. 20° C. and a relative humidity of 95–100% and placed in a greenhouse at ca. 22° C.

Evaluation of the development of Rustpustules took place 12 days after infection.

Activity against Phytophthora infestans on tomato plants (a) Residual-curative activity Three week old tomato plants were infected with a suspension of fungal sparangia. After incubation for 22 hours in a humidity chamber at 90–100% relative humidity and 20° C. the plants were sprayed with a broth containing 0.06% of the compound to be tested. After drying of the spray-coating the plants were returned to the humidity chamber. Evaluation of fungal attack was made 5 days after infection.

(c) Systemic activity

Three week old tomato plants were watered with broth containing the test compound to give a concentration thereof of 0.006% with respect to soil volume. Care was taken to prevent contact between the broth and the aerial plant parts. After 48 hours the plants were infected with a suspension of fungal sporangia. Evaluation of fungal attack was made after 5 days incubation of the infected plants at 90–100% relative humidity and 20° C.

Activity against Xanthomonas oryzae on rice (a) Residual-protective activity

Three week old rice plants of the variety "caloro" or "S6" were sprayed with a broth containing 0.06% of the compound to be tested.

After drying for one day the plants were placed in a controlled climate room at 24° and 75–85% relative humidity and infected by removing the leaf tips with scissors previously dipped in a suspension of Xanthomonas oryzae. After 10 days of incubation in the same room diseased leaves withered, curled and became necrotic. The extent of these symptoms was used to evaluate the activity of the test compound.

(b) Systemic activity

Three week old rice plants of the variety "Caloro" or "S6" were watered with a broth containing the test compound to give a concentration thereof of 0.006% with respect to soil volume. Care was taken to prevent contact between the broth and the aerial plant parts. Three days after treatment the plants were placed in a controlled climate room at 24° C. and 75–85% relative humidity and infected by removing the leaf tips with scissors previously dipped in a suspension of Xanthomonas oryzae. After 10 days of incubation in the same room diseased leaves withered, curled and became necrotic. The extent of these symptoms was used to evaluate the activity of the test compound.

Activity against Xanthomonas vesicatoria on paprika (a) Residual-protective activity Three week old greenhouse raised paprika plants of the variety "California Wonder" were sprayed with a broth containing 0.06% of the compound to be tested. After drying for one day the plants were placed in a controlled climate room at 26° C. and 95–100% relative humidity and infected by spraying the underside of the leaves with a standardised suspension of Xanthomonas vesicatoria. After 6 days of incubation the disease appeared in the form of round, initially watery subsequently necrotic, bright spots. The extent of these symptoms was used to evaluate the activity of the test compound.

(b) Systemic activity

Three week old greenhouse raised paprika plants were watered with a broth containing the test compound to give a concentration thereof of 0.006% with respect to soil volume. Care was taken to prevent contact between the broth and the aerial plant parts. Three days after this treatment the plants were placed in a controlled climate room at 26° C. and 95–100% relative humidity and infected by spraying the underside of the leaves with a standardised suspension of Xanthomonas vesicatoria. After 6 days of incubation the disease appeared in the form of round, initially watery subsequently necrotic, bright spots. The extent of these symptoms was used to evaluate the activity of the test compound.

Activity against Helminthosporium gramineum

Wheat grains were contaminated with a sporal suspension of the fungus, dried and dressed with a broth containing the test substance to give a concentration thereof of 0.06% with respect to the weight of seed grains. After 10 days the grains were placed on suitable agar dishes and after two days the development of fungal colonies round the grains was determined.

Activity against Cercospora arachidicola on ground-nut plants.

10–15 cm high ground-nut plants were sprayed with a broth containing 0.02% of the compound to be tested and after 48 hours infected with a suspension of fungal conidia. The infected plants were incubated for 72 hours at ca. 21° C. and high humidity and then placed in a greenhouse until the appearance of typical leafspots on the control plants. Evaluation of the fungal attack took place 12 days after infection on the basis of the number and size of leaf spots.

USE EXAMPLE 29

The compounds of the Formula I exhibited a good fungicidal and bactericidal activity. The following compounds, amongst others, inhibited the fungal attack to less than 20% in comparison with untreated but infected controls (=100%).

against Puccinia graminis; compounds of Examples 2, 6, 21 and 22.

against Phytophthora infestans; compounds of Examples 6, 8, 21 and 22.

against Xanthomonas oryzae; compounds of 2, 6, 21 and 22.

against Xanthomonas vesicatoria; compounds of Examples 2, 6, 21 and 22.

against Helminthosporium gramineum; compounds of Examples 2 and 22.

against Cercospora arachidicola; compound of Example 2.

EXAMPLE 30

Dusts

The following substances are used to prepare (a)

5% and (b) a 2% dust:

(a)

5 parts of active substance
95 parts of talc;

(b)

2 parts of active substance
1 part of highly dispersed silicic acid
97 parts of talc.

The active substances are mixed with the carriers and ground and in this form can be processed to dusts for application.

EXAMPLE 31

Granulate

The following substances are used to prepare a 5% granulate:

5 parts of active substances
0.25 part of epichlorohydrin
0.25 part of cetyl polyglycol ether
3.25 parts of polyethylene glycol
91 parts of kaolin (particle size 0.3–0.8 mm).

The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo. Such a microgranulate may be used for example in combating soil diseases.

EXAMPLE 32

Wettable powders

The following constituents are used to prepare (a) a 70%, (b) a 40%, (c) and (d) a 25% and (e) a 10% wettable powder:

(a)

70 parts of active substance
5 parts of sodium dibutylnaphthylsulphonate
3 parts of naphthalenesulphonic acid/phenolsulphonic acid/formaldehyde condensate (3:2:1)
10 parts of kaolin
12 parts of Champagne chalk (b)

40 parts of active substance
5 parts of sodium ligninsulphonate
1 part of sodium dibutylnaphthalenesulphonic acid
54 parts of silicic acid (c)

25 parts of active substance
4.5 parts of calcium ligninsulphonate
1.9 parts of Champagne chalk/hydroxyethyl cellulose mixture (1:1)
1.5 parts of sodium dibutylnaphthalenesulphonate
19.5 parts of silicic acid
19.5 parts of Champagne chalk
28.1 parts of kaolin (d)

25 parts of active substance
2.5 parts of isooctylphenoxy-polyethylene-ethanol
1.7 parts of a Champagne chalk/hydroxyethyl cellulose mixture (1:1)
8.3 parts of sodium aluminium silicate
16.5 parts of kieselguhr
46 parts of kaolin (e)

10 parts of active substance
3 parts of a mixture of the sodium salts of saturated fatty alcohol sulphates
5 parts of naphthalenesulphonic acid/formaldehyde condensate
82 parts of kaolin.

The active substances are intimately mixed in suitable mixers with the additives and ground in appropriate mills and rollers. Wettable powders of excellent wettability and suspension power are obtained. These wettable powders can be diluted with water to give suspensions of the desired concentration and can be used in particular for leaf application.

EXAMPLE 33

Emulsifiable concentrates

The following substances are used to prepare a 25% emulsifiable concentrate:
25 parts of active substance
2.5 parts of epoxidised vegetable oil
10 parts of an alkylarylsulphonate/fatty alcohol polyglycol ether mixture
5 parts of dimethyl formamide
57.5 parts of xylene.

By diluting such a concentrate with water it is possible to prepare emulsions of the desired concentration, which are especially suitable for leaf application.

What we claim is:

1. A compound having the formula:

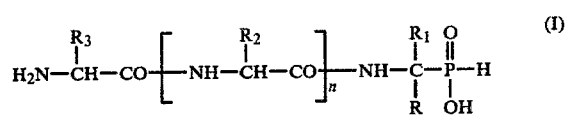

or the corresponding zwitterion form in which R and $R_1$ may be the same or different and each can be hydrogen, deuterium, lower alkyl, lower alkyl substituted by halogen, hydroxy, lower alkoxy, mercapto, carboxyl, S-substituted dithio groups, $-NR_4R_5$ wherein $R_4$ and $R_5$ can be the same or different and each is hydrogen, lower alkyl, guanidino or phenyl, or $R_4$ and $R_5$ together may form a polymethylene chain containing up to 6 carbon atoms which may be interrupted by oxygen or nitrogen, or phenoxy or phenoxy substituted by hydroxy or halogen, lower alkenyl, lower alkynyl, $C_3$–$C_7$ cycloalkyl, phenyl, phenyl substituted by loweralkyl, hydroxy, lower alkoxy or halogen, aziridine, oxetane, thiophene, furan, pyridine, azepine, isoxazole, thiazole, pyrimidine, diazepine, thiadiazole, triazole, triazine, imidazole or indole, a lower alkyl group substituted by a $C_3$–$C_7$ cycloalkyl radical, a lower alkyl group substituted by a phenyl, tolyl, xylyl, ethylphenyl, propylphenyl, isopropylphenyl, butylphenyl, isobutylphenyl, see-butylphenyl, tert-butylphenyl, or naphthyl radical, a lower alkyl group substituted by aciridine, oxetane, thiophene, furan, pyridine, azepine, isoxazole, thiazole, pyrimidine, diazepine, thiadiazole, triazole, triazine, imidazole or indole, or R and $R_1$ together form a polymethylene chain optionally interrupted by an oxygen, nitrogen or sulphur atoms, or $R_1$ represents, together with the C(R)-N< residue to which it is attached, the atoms required to complete a pyrrolidine, 4-hydroxypyrrolidine or pyrrolidone ring; and $R_2$ and $R_3$ may be the same or different and each can be hydrogen, lower alkyl lower alkyl substituted by halogen, hydroxy, lower alkoxy, mercapto, carboxyl, S-substituted dithio groups, $-NR_4R_5$ wherein $R_4$ and $R_5$ can be the same or different and each is hydrogen, lower alkyl, guanidino or phenyl, or $R_4$ and $R_5$ together may form a polymethylene chain containing up to 6 carbon atoms which may be interrupted by oxygen or nitrogen, or phenoxy or phenoxy substituted by hydroxy or halogen, $C_3$–$C_7$ cycloalkyl, phenyl, phenyl substituted by lower alkyl, hydroxy, lower alkoxy or halogen, or lower alkyl substituted by a $C_3$–$C_7$ cycloalkyl radical, lower alkyl substituted by aziridine, oxetane, thiophene, furan, pyridine, azepine, isoxazole, thiazole, pyrimidine, diazepine, thiadiazole, thiazole, triazine, imidazole or indole,;
aziridine, oxetane, thiophene, furan, pyridine, azepine, isoxazole, thiazole, pyrimidine, diazepine, thiadiazole, triazole, triazine, imidazole or indole,;
or $R_2$ and $R_3$, independently, together with the >C(H)-N< residue to which each is attached, by each represent the atoms required to complete a pyrrolidine, 4-hydroxypyrrolidine or pyrrolidone ring; and n is 0, 1, 2 or 3; as well as the esters thereof with alcohols selected from the group consisting of lower alkyl alcohols, aralkyl alcohols, phenols, alkanoyloxymethanols, amino-lower alkanoyloxymethanols, 3-hydroxyphthalide and 5-indanol; salts of the compounds of formula I, with acids or bases; and all optical isomers thereof.

2. The compound of formula I as claimed in claim 1 wherein R is hydrogen or deuterium; $R_1$ is hydrogen, deuterium lower alkyl lower alkyl substituted by halogen, hydroxy, lower alkoxy, mercapto, carboxyl, S-substituted dithio groups, —NR$_4$R$_5$ wherein R$_4$ and R$_5$ can be the same or different and each is hydrogen, lower alkyl, guanidino or phenyl, or R$_4$ and R$_5$ together may form a polymethylene chain containing up to 6 carbon atoms which may be interrupted by oxygen or nitrogen, or phenoxy or phenoxy substituted by hydroxy or halogen,, or R$_1$ represents, together with the >CR-N< residue to which it is attached, the atoms required to complete a 2-pyrrolidinyl group or homo-2-pyrrolidinyl group; R$_2$ and R$_3$ may be the same or different and each is hydrogen, lower alkyl, lower alkyl substituted by halogen, hydroxy, lower alkoxy, mercapto, carboxyl, S-substituted dithio groups, —NR$_4$R$_5$ wherein R$_4$ and R$_5$ can be the same or different and each is hydrogen, lower alkyl, guanidino or phenyl, or R$_4$ and R$_5$ together may form a polymethylene chain containing up to 6 carbon atoms which may be interrupted by oxygen or nitrogen, or phenoxy or phenoxy substituted by hydroxy or halogen, phenyl or phenyl substituted by lower alkyl, hydroxy, lower alkoxy or halogen and n is 0, 1, 2 or 3; as well as the esters with alcohols selected from the group consisting of lower alkyl alcohols, aralkyl alcohols, phenols, alkanoyloxymethanols, amino-lower alkanoyloxymethanols, 3-hydroxyphthalide and 5-indanol, or salts with acids or bases; and all optical isomers thereof.

3. The compound of formula I as claimed in claim 1 wherein R is hydrogen; R$_1$ is hydrogen, methyl, isopropyl, 2-carboxyethyl or 2-methylthioethyl; R$_2$ and R$_3$ may be the same or different and each can be hydrogen, methyl, isopropyl, 2-methylthioethyl, -aminobutyl, benzyl, or R$_2$ and R$_3$ represents together with the >C(R)-N< residue to which it is attached the atoms required to complete the pyroglutamyl residue; and n is 0, 1, 2, or 3; as well as the esters thereof with alcohols selected from the group consisting of lower alkyl alcohols, aralkyl alcohols, phenols, alkanoyloxymethanols, amino-lower alkanoyloxymethanols, 3-hydroxyphthalide and 5-indanol and salts with acids or bases; and all optical isomers thereof.

4. The compound of formula I as claimed in claim 2 wherein R$_1$ is hydrogen or methyl.

5. The compound of formula I as claimed in claim 4 wherein R is hydrogen; R$_1$ is methyl; R$_2$ and R$_3$ are hydrogen or methyl; and n is 0, 1, 2 or 3; and the esters threof with alcohols selected from the group consisting of lower alkyl alcohols, aralkyl alcohols, phenols, alkanoyloxymethanols, amino-lower alkanoyloxymethanols, 3-hydroxyphthalide and 5-indanol; salts of the compounds of formula I with acids or bases; and all optical isomers thereof.

6. A mixture of the diasteroemers of 1-(D-alanylamino)-ethanephosphonous acid and the diastereomers of 1-(L-alanylamino)-ethanephosphonous acid.

7. Mixtures of diastereomers of 1-(L-alanylamino)-ethane phosphonous acid.

8. 1R-1-(L-alanylamino)-ethanephosphonous acid.

9. 1S-1-(L-alanylamino)-ethanephosphonous acid.

10. Mixtures of diastereomers of 1-(L-alanyl-L-alanylamino)-ethanephosphonous acid.

11. 1R-1-(L-alanyl-L-alanylamino)-ethanephosphonous acid.

12. 1R-1-(L-alanyl-L-alanyl-L-alanylamino)ethanephosphonous acid.

13. 1R-1-(L-alanyl-L-alanyl-L-alanyl-L-alanylamino)-ethanephosphonous acid.

14. 1-(L-alanylamino)-2-methylpropanephosphonous acid.

15. [(1-(—)]-1-(L-alanylamino)-2-methylpropanephosphonous acid.

16. [(1-(+)]-1-(L-alanylamino)-2-methylpropanephosphonous acid.

17. 1RS-1-(L-alanylamino)-3-carboxypropanephosphonous acid.

18. Mixtures of diastereomers of 1-(L-valylamino)ethanephosphonous acid.

19. 1RS-1-(L-phenylalanylamino)ethanephosphonous acid.

20. 1RS-1-(L-lysylamino)ethanephosphonous acid.

21. 1RS-1-(L-methionylamino)-2-methylpropanephosphonous acid.

22. 1-(D-alanylamino)-ethanephosphonous acid.

23. The racemate of 1-glycylaminoethanephosphonous acid.

24. 1R-1-(glycylamino)-ethanephosphonous acid.

25. 1-glycylaminomethanephosphonous acid.

26. L-alanylaminomethanephosphonous acid.

27. 1-(L-pyroglutamylamino)-ethanephosphonous acid.

28. An antimicrobial composition comprising an effective amount of a compound of formula I, according to claim 1 together with a suitable carrier.

29. An antimicrobial composition as claimed in claim 28 which is effective against the growth of plantpathogenic bacteria and fungi.

30. A method of combatting plant pathogenic bacteria and fungi which comprises applying to their habitat an effective amount of a compound of formula I according to claim 1.

31. A method as claimed in claim 30 wherein bacteria of the Pseudomonas and Xanthomonas variety are combatted.

32. A method as claimed in claim 30 for protection of rice plants from the attack of Xanthomonas oryzae which comprises applying to said plants or to their growing area an effective amount of 1R-1-(L-alanylamino)-ethanephosphonous acid or 1-glycylaminoethanephosphonous acid.

33. A compound having the formula

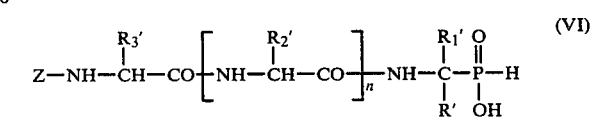

wherein R', R'$_1$, R'$_2$ and R'$_3$ have the meanings defined in claim 1 for the substituents R, R$_1$, R$_2$ and R$_3$, respectively, except that any amino group, hydroxy group or any other functional group which is present is in protected form, Z is hydrogen or a protecting group as used for an amino group, and n is as defined in claim 1.

* * * * *